Figure 1:
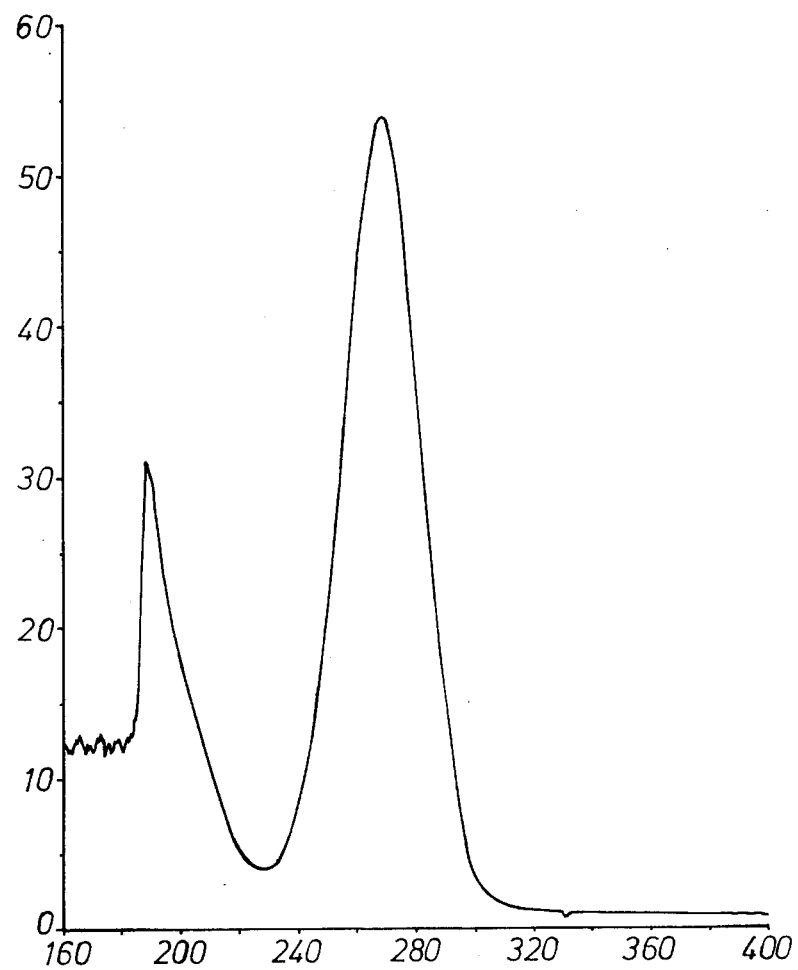

United States Patent [19]

Bauer et al.

[11] 4,031,207

[45] June 21, 1977

[54] ANTIBIOTIC

[75] Inventors: Klaus Bauer; Werner Frommer; Wilfried Kaufmann; Georg Metzger; Martin Scheer; Delf Schmidt; Theo Schröder, all of Wuppertal; Dietmar Schäfer, Marburg, Lahn, all of Germany

[73] Assignee: Bayer Aktiengesellschaft, Germany

[22] Filed: Feb. 26, 1976

[21] Appl. No.: 661,545

[30] Foreign Application Priority Data

Mar. 8, 1975 Germany .......................... 2510161

[52] U.S. Cl. .............................. 424/118; 195/80 R
[51] Int. Cl.² ........................................ A61K 35/74
[58] Field of Search ................... 424/118; 195/80 R

[56] References Cited

UNITED STATES PATENTS 3,824,305  7/1974  Hamill et al. ...................... 424/118

Primary Examiner—Jerome D. Goldberg

[57] ABSTRACT

Strains of Actinoplanes produce an antibiotic substance upon aerobic cultivation. The antibiotic is soluble in water with a pronounced band in the UV absorption spectrum at 267 nm. Methods for preparing and using the antibiotic, both therapeutically and for promoting livestock growth, and composition adapted for these uses are described.

9 Claims, 4 Drawing Figures

ANTIBIOTIC

The present invention relates to a new antibiotic, to a process for its preparation from Actinoplanaceae strains and to its use, both as an antimicrobial agent in human and veterinary medicine and as an agent for promoting growth and increasing feedstuff utilization in animals.

It is known that a number of substances of microbial origin possess antimicrobial actions. Some of these antibiotics have a limited spectrum of action as well as other disadvantages. $\beta$-Lactam antibiotics for example are frequently inactivated by penicillinase. Various other antibiotics of microbial origin, such as chloramphenicol, tetracyclines and streptomycin, exhibit undesirable side-effects.

It has now been discovered that new antibiotics can be obtained when the Actinoplanes strains SE 73 or SE 73/B are cultured, individually or conjointly, under aerobic conditions, in a culture medium containing assimilable sources of carbon, nitrogen and minerals.

Two major antibiotic substances are formed under these conditions. One of these is sparingly soluble in water and has a UV absorption spectrum which exhibits a pronounced band at $\lambda = 307$ mm. This antibiotic is described and claimed in our copending U.S. patent application Ser. No. 661,544. The second antibiotic which is the subject of the present invention has a UV absorption spectrum with a pronounced band at $\lambda = 267$ nm.

The antibiotic of the present invention a. consists of carbon, hydrogen and oxygen;
b. is soluble in water, lower alcohols, chloroform and acetone and is sparingly soluble in diethyl ether, petroleum ether and cyclohexane;
c. is neutral and does not migrate on electrophoresis;
d. eliminates reducing sugars on acid hydrolysis;
e. exhibits a pronounced band at 267 nm in the UV spectrum; and
f. has an $[\alpha]_D^{20} = -32.97°$ (1%, methanol).

Samples of the antibiotic have yielded the following elementary analysis:

C = 50.8%; H = 7.2%; O = 42%.

This corresponds to the empirical formula: $C_{58}H_{98}O_{36}$ although, as is known the margin of error in the elementary analysis ($\pm 1.0\%$) for large molecules does not always enable an accurate empirical formula to be calculated [R. B. Woodward, Angew. Chem. 69, page 50–51 (1957).].

Typical UV, $^{13}$C-NMR, IR and $^1$H-NMR spectra of the antibiotic are shown in FIGS. 1 to 4, respectively, of the accompanying drawings. There are described in more detail hereafter.

As already noted above, the antibiotic is soluble in water, lower alcohols ($C_1$–$C_4$), chloroform and acetone, moderately soluble in ethyl acetate, and sparingly soluble in diethyl ether, petroleum ether and cyclohexane.

The molecular weight is in the range 1,300 to 1,390 and very probably is at or about 1,354.

The sensitivity to acid is characteristic of the molecule. At pH 2 and room temperature of 18° to 22° C the antibiotic activity falls to zero in the source of 1 hour and the characteristic band in the UV spectrum at 267 nm disappears. The antibiotic is also decomposed by alkali. On heating in N/10 sodium hydroxide solution to 100° C in the course of 30 minutes, a compound is formed which exhibits only end absorption in the ultraviolet range. Compared with the starting antibiotic, the product has a reduced, albeit distinct, in vitro action against Gram negative bacteria.

The antibiotic according to the invention is a neutral substance which does not migrate on electrophoresis. On acid hydrolysis, as for example with aqueous 10% by weight sulphuric acid at 80° C, reducing sugars are eliminated. Due to this fact, it is easily possible to render the antibiotic visible in thin layer chromatography on a silica gel plate with acid sugar reagents, such as, for example, anisaldehydesulphuric acid, benzidine-trichloroacetic acid or thymolsulphuric acid. Spraying with 10% strength sulphuric acid and heating at 80° C for ten minutes also gives a blue-grey coloration on the plate. The latter reagent has been proposed for characteristic identification of macrolide antibiotics [E. Stahl, Dunnschicht-Chromatographie (Thin Layer Chromatography), 2nd Edition, 1967, page 546].Table 1 gives the $R_F$ values of the antibiotic on silica gel plates (Merck, Darmstadt) with various running agents.

Table 1

| Running agent (parts by volume) | | $R_F$ value |
| --- | --- | --- |
| 5:95 | methanol:chloroform | 0.025 |
| 1:4 | methanol:chloroform | 0.49 |
| 1:1 | methanol:chloroform | 0.755 |
| 100% | methanol | 0.715 |
| 60:20:20 | n-butanol:glacial acetic acid:water | 0.470 |

When comparing the present antibiotic to known antibiotics, one can exclude the nitrogen-containing aromatic antibiotics which are insoluble in chloroform since the present antibiotic consists only of carbon, hydrogen and oxygen and contains no nitrogen. The content of reducible sugars which can be removed by hydrolysis, the solubility pattern, and the coloration with 10% strength sulphuric acid indicate a certain similarity to the macrolide antibiotics, of which a few nitrogen-free representatives are known. However, in contrast to the present antibiotic, the macrolides are primarily active against Gram positive organisms, not against Gram negative organisms; see e.g. Keller-Schierlein, Fortschritte der Chemie organischer Naturstoffe 30, page 314 (1973). Furthermore, no known macrolide antibiotic absorbs at 267 nm; see Gottlieb and Shaw, Antibiotics II (1967) 159.

The antibiotic is produced by the above mentioned Actinoplanes strains and can be readily isolated from the culture medium in good yield. The antibiotic exhibits powerful antimicrobial, especially antibacterial, action against Gram negative pathogens without exhibiting the associated disadvantages of known antibiotics. The compound can thus be used therapeutically and prophylactically as an antibiotic as well as for promoting growth and improving the feed-stuff utilization in animals.

The strains which can be used according to the invention, Actinoplanes species SE-73 and SE-73/B, belong to the class of Schizomycetes, the order of Actinomycetales, the family of Actinoplanaceae and the genus Actinoplanes. The SE-73 strain was isolated from soil and the SE-73/B strain was obtained as a spontaneous mutant of the SE-73 strain. Both strains have the following characteristics:

The mycelium is 0.3 to 1.3 $\mu$ wide and is branched. The sporangia are of irregular shape, usually approximately spherical in outline, but with a gibbous surface and have a diameter of 5 to 18 μ. The spores are spherical to ellipsoidal and flagellated, move rapidly and have a diameter of 0.7 to 1.3 μ. They are arranged in the sporangium in the form of curved and convoluted chains.

The culture characteristics on various culture media (observed after 14 days at a growth temperature of 20° to 30° C) can be seen from the table given below:

Table 2

| | | |
|---|---|---|
| Czapek agar | G | good to very good |
| | SM | orange |
| | SP | pale brownish-yellow |
| | Spg. | +, mycelium surface slightly frosted |
| CPC casamino-peptone-Czapek agar | G | good to very good |
| | SM | orange to orange-brown |
| | SP | brown |
| | Spg. | ++, mycelium surface slightly frosted |
| lactose agar | G | good to very good |
| | SM | orange |
| | SP | golden brown |
| | Spg. | ++, mycelium surface slightly frosted |
| | casein | peptonized |
| tyrosine agar | G | moderate to good |
| | SM | brown |
| | SP | brown |
| | Spg. | −, some of the mycelium surface slightly frosted |
| | tyrosine | crystals not dissolved |
| melanin formation | | positive |
| milk peptonization | | positive |

G = growth
SM = substrate mycelium
SP = soluble pigment
Spg. = formation of sporangia
− = lack
+ = marked presence
++ = very marked presence The SE-73/B strain differs from the SE-73 strain in that it produces a greater amount of the antibiotic.

The process can be carried out with the aid of solid, semi-solid or liquid culture media. Preferably, aqueous liquid culture media are used. Inoculation of the culture media is carried out according to generally customary methods, for example via small slanted tubes or flask cultures. The culture is conducted under aerobic conditions according to customary methods, such as using shaken cultures, for example in shaking flasks, aerated cultures or submersed cultures. The cultivation preferably performed by the aerobic submersed method in aerated fermenters, for example in customary submersed fermentation tanks. It is possible to carry out the culture continuously or discontinuously but the discontinuous method is generally used. The culture can be carried out in any culture medium useful for the cultivation of microorganisms of the order to Actinomycetales. The culture medium must contain one or more sources of assimilable carbon and nitrogen as well as mineral salts. These products can be present in the form of individual constituents or in the form of complex mixtures, such as, in particular, biological products of various origins. Any of the customary sources of carbon can be used such as starch, molasses, whey powder, dextrin, sugars, such as sucrose, maltose, glucose or lactose, sorbitol and glycerol. Similarly, the customary organic and inorganic sources of nitrogen can be used such as soya bean flour, cottonseed flour, lentil flour, pea flour, soluble and insoluble vegetable proteins, corn steep liquor, yeast extract, peptones and meat extract as well as ammonium salts and nitrates, for example $NH_4Cl$, $(NH_4)_2SO_4$, $NaNO_3$ and $KNO_3$.

Mineral ions which should be present in the culture medium include $Mg^{++}$, $Na^+$, $K^+$, $Ca^{++}$, $NH_4^+$, $Cl^-$, $SO_4^{--}$, $PO_4^{---}$ and $NO_3$ as well as ions of the customary trace elements, such as Cu, Fe, Mn, Mo, Zn, Co and Ni. If the sources of carbon or nitrogen or the water used to not supply or contain these salts and trace elements at an adequate level, it is appropriate to supplement the culture medium accordingly. The composition of the culture media can be varied within wide ranges. It is often advantageous to supply relatively small concentrations of the soluble constituents of the nutrient solution at the start of the cultivation and then, in the coursse of the first three days of cultivation, to add these constituents in fractions, in the form of a sterile, relatively concentrated solution, to the culture batch by means of relatively frequent additions.

The pH value of the growing culture should be kept between about 6 and about 8, especially between 6.5 and 7.5. Too great a drop in the pH into the acid range can be avoided by additions of an organic or inorganic base, preferably calcium carbonate. As is customary in fermentation technology, the pH can also be regulated automatically by injecting a sterile organic or inorganic acid, for example sulphuric acid, or sterile alkaline solution, for example sodium hydroxide, at intervals into the culture solution.

To ensure that the microorganisms are adequately brought into contact with oxygen and the nutrient substances, shaking or stirring should be maintained.

The culture temperature is from about 20 to about 40° C, preferably between 25° and 35° C, and especially about 28° C. The culture period can be varied greatly and the composition of the culture medium and the culture temperature play a role here. The optimum conditions for a particular case can be readily determined by one skilled in the art by conventional methods. Generally the amount of the antibiotic which accumulates in the culture broth reaches its maximum about 2 to about 12, usually 5 to 8, days after the start of culture.

As is general in the case of microbiological processes, contamination of the culture media by foreign bodies should be avoided. For this purpose, the customary precautionary measures are taken, such as sterilization of the culture media, of the culture vessels and of the air required for aeration.

If foam forms in an undesirable amount during the cultivation, the customary chemical foam-suppressants, for example liquid fats and oils, oil-in-water emulsions, paraffins, higher alcohols, such as octodecanol, silicone oils, polyoxyethylene compounds and polyoxypropylene compounds, can be added. Foam can also be suppressed or eliminated with the aid of the customary mechanical centrifugal devices.

The antibiotic can be isolated from the mycelium and/or from the culture medium and purified by customary extraction, precipitation and/or chromatographic processes. In many cases a high degree of purification is not required since the impurities which may be present do not have an adverse effect on antibiotic activity. In all isolation and purification operations, care should be taken that pH values of 7.0 or above, preferably between 7.0 and 9.0, are maintained. In order to increase the pH value, it is possible to use inorganic and organic bases, for example ammonia, alkali metal hydroxides and alkaline earth metal hydroxides, alkali metal carbonates and bicarbonates, and alkaline earth metal carbonates and bicarbonates, for example KOH, NaOH, $Na_2CO_3$, $NaHCO_3$, $CaCO_3$, trialkylamines, such as triethylamine, morpholine and pyridine.

In order to determine the fractions in which the antibiotic is present in the highest concentration or purity, one can employ the customary physicochemical methods, for example measure the UV band at the characteristic wave length, determine $R_F$ values or, preferably, assay antimicrobial activity. Bioassay against *Escherichia coli* such as ATCC 9637 with the aid of the customary plate test, see e.g. Klein, Bakteriologische Grundlagen der chemotherapeutischen Laboratoriumspraxis, Springer-Verlag, Göttingen (1957), pp. 86 et seq., is particularly advantageous.

When a liquid aqueous culture medium is used, isolation and purification can be carried out as follows:

A water-miscible organic solvent is added to the culture broth, including the mycelium, and is mixed well. The active compound is then extracted from the mycelium and in many cases clarification of the culture broth is also achieved. Solvents which can be used include lower alkanols of 1 to 4 carbon atoms, such as methanol, ethanol, propanol, isopropanol and t.-butanol; dimethylformamide, tetrahydrofuran, acetone and the like. Acetone is preferred. The amount of solvent can be varied within wide limits but generally addition of a volume about equal to that of the culture broth is satisfactory. The undissolved constituents which include mycelium, precipitated proteins and the like are then removed by filtration, centrifuging, normal settling or the like procedure. The aqueous-organic solution is concentrated in vacuo to about the volume of the culture medium employed. If necessary, the pH value is adjusted to a value greater than 7.0, for example 9.0, by means of a base such as sodium hydroxide. The solution thus obtained is hereafter designated "solution I".

The antibiotic can be isolated, and, if desired, purified, with the aid of customary extraction, precipitation, and/or chromatographic methods. Chromatography can be carried out in the form of column chromatography or preparative thin layer chromatography. Adsorbents which can be used are all customary non-acidic inorganic or organic adsorbents, such as, for example, aluminum oxide, silica gel, magnesium silicate, active charcoal, cellulose, cellulose derivatives, crosslinked dextran derivatives, synthetic resins such as polyamides, derivatives of polyamides such as acetylated polyamide, and the like. Running agents which can be used for preparative thin layer chromatography include any solvent or solvent mixtures in which the antibiotic is soluble. A mixture of 5:1 chloroform:methanol (by volume) is highly satisfactory. Solvents and solvent mixtures in which the antibiotic is soluble can also be used as running agents for column chromatography, as for example carbon tetrachloride, methylene chloride and, preferably, chloroform may be mentioned as examples. Extraction methods, optionally in combination with chromatographic and precipitation methods, can also be used for isolation of the antibiotic. When carrying out extractions, care must of course be taken that, depending on whether the antibiotic is to be present in the aqueous or organic phase, the extraction agents are so selected that the antibiotic is sparingly soluble or readily soluble therein, respectively.

Solution I can thus be extracted with water-immiscible organic solvents by customary methods such as shaking, countercurrent method and the like with extraction agents, as for example esters such as ethyl acetate and butyl acetate; higher alcohols such as amyl alcohols; water-immiscible ketones such as methyl isobutyl ketones; and chlorinated hydrocarbons such as chloroform, methylene chloride and carbon tetrachloride. Preferably ethyl acetate or butyl acetate, especially ethyl acetate, is used.

If ethyl acetate and/or butyl acetate is employed for the extraction of solution I, the organic phase is discarded, the antibiotic being present in the aqueous phase. The aqueous phase thus obtained is saturated with an inert organic salt customarily used for such purposes, for example NaCl, KCl, $Na_2SO_4$ and/or $MgSO_4$, in order to facilitate the subsequent extraction. The amount of salt added is not critical and naturally depends on the volume of solution and solubility of the salts, both of which can be easily determined. The aqueous solution is next extracted with a solvent which is immiscible with water and in which the antibiotic is soluble, such as are discussed above in connection with the explanation of the extraction of solution I; however no esters can be used. The organic phase is concentrated to, for example, about 1/10 to 1/30 of the original volume and the antibiotic is then precipitated according to customary methods by adding an organic precipitant (solvent) in which the antibiotic is sparingly soluble, as for example diethyl ether or a straight, branched chain or cyclic saturated hydrocarbon such as petroleum ethers, n-hexane or cyclohexane. For additional purification, the precipitate is dissolved in water and the crude antibiotic obtained by evaporation of the water, preferably by freeze drying. The crude antibiotic can be highly purified, if desired, by chromatographic methods such as column chromatography or preparative thin layer chromatography utilizing adsorbents discussed above.

If in place of ethyl acetate or butyl acetate a solvent such as carbon tetrachloride is used, the antibiotic will be present in the organic phase. This is concentrated to about 1/10 to 1/30 of the original volume and the antibiotic is precipitated by addition of an organic precipitant in which the antibiotic is sparingly soluble such as an ether or hydrocarbon, as discussed above. The precipitate is dissolved in water and this solution is then freeze-dried. The resulting product can, if desired, be extracted with ethyl acetate or butyl acetate, in which undesired impurities are soluble, with the organic solution being discarded and the product further purified by customary chromatographic methods as discussed above.

As already mentioned above, the antibiotic can also be purified by fractional precipitation from a solution of the crude product in an organic solvent such as acetone, carbon tetrachloride, chloroform or methylene chloride with the aid of the organic precipitants discussed above.

The new Actinoplanes strains SE-73 and SE-73/B have been deposited as follows:

| | SE-73 | SE-73/B |
|---|---|---|
| American Type Culture Collection | No. 31,058 | No. 31,060 |
| Centralbureau voor Schimmelcultures | 432.74 | 434.74 |
| Fermentation Research Institute (Japan) | 2,669 | 2,671 |

Referring now to the drawings;

FIG. 1 presents the ultraviolet absorption spectrum of the antibiotic, the abscissa being wavelength (nm) and the ordinate being % absorption.

$\lambda$ max = 265 nm (C = 0.0091% in methanol)

$[E^{1\%}/cm]_{265\ nm} = 164$

Figure 2:
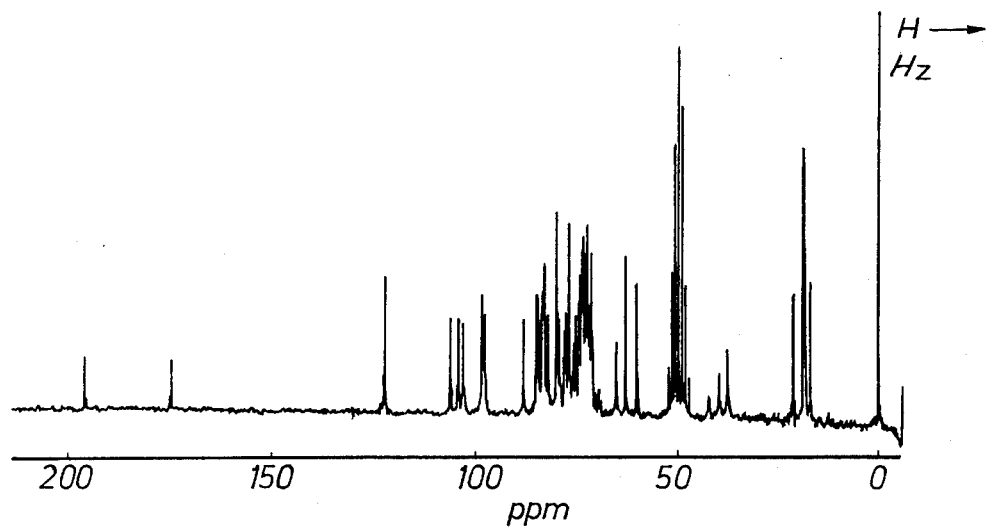

FIG. 2 presents the $^{13}$C nuclear resonance spectrum, measured in a solution of the antibiotic in deuterized methanol using tetramethylsilane as an internal standard in the same solution on a Varian XL-100 spectrometer (15 inches) at 25.2 MHz with proton noise decoupling.

Figure 3:
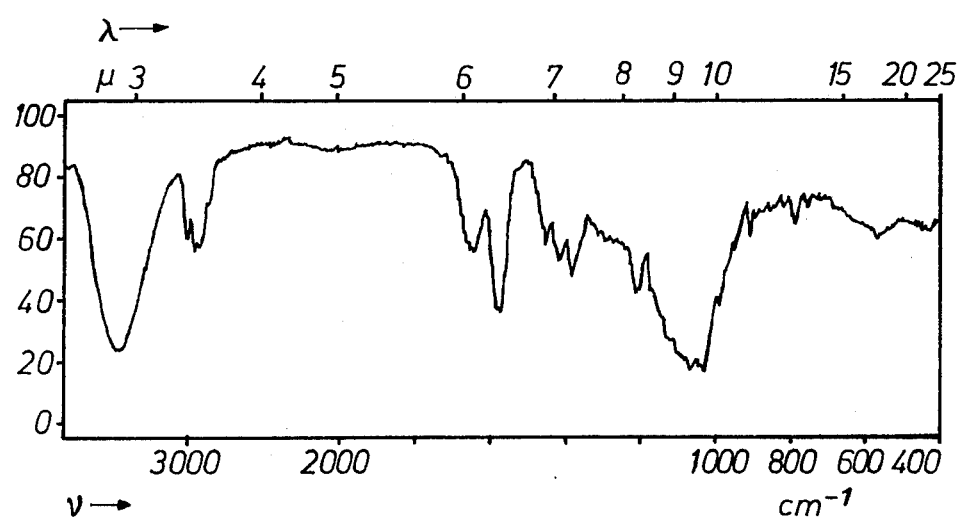

FIG. 3 gives the IR absorption spectrum of the antibiotic in KBr, the abscissa being wavelength (cm$^{-1}$) and the ordinate being % absorption.

Absorption bands are shown at the following wavelengths:

Table 3

| Band frequency cm$^{-1}$ | Intensity | Band frequency cm$^{-1}$ | Intensity |
|---|---|---|---|
| 3440 | s | 1290 | w |
| 2960 | m | 1200 | m |
| 2920 | m | 1060 | s |
| 2850 | m | 1020 | s |
| 1630 | m | 985 | m |
| 1570 | s | 940 | m |
| 1445 | m | 905 | m |
| 1405 | m | 780 | m |
| 1375 | m | 750 | m |
| 1310 | w | | |

The IR band intensities are designated as s, m and w. An s band has at least ⅔rds of the intensity of the strongest band in the spectrum, an m band has an intensity in the range between ⅓rd and ⅔rds that of the strongest band and a w band has less than ⅓rd of the intensity of the strongest band. These estimates are made on the basis of the percentage transmission.

Figure 4:
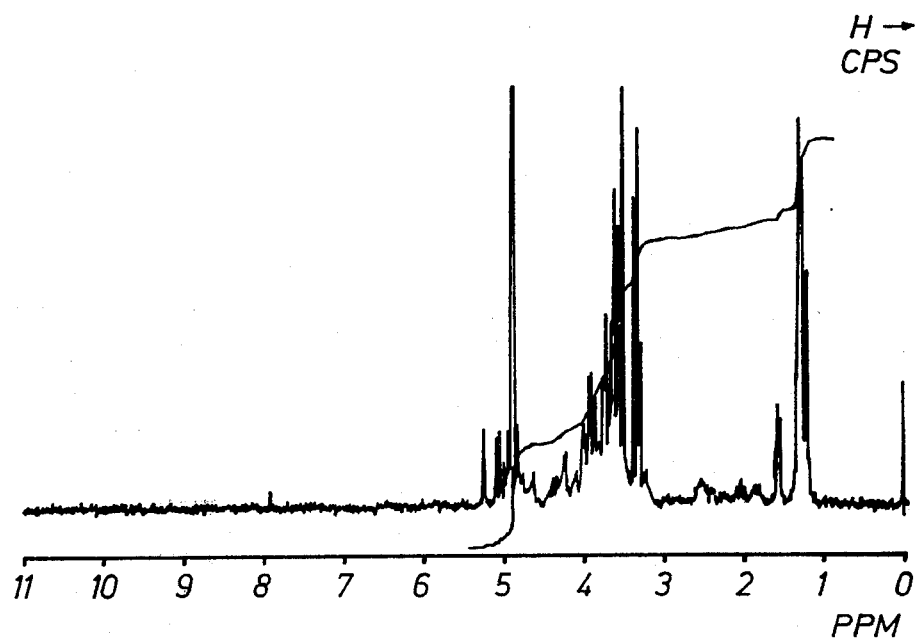

The 220 MHz $^1$H nuclear resonance spectrum is shown in FIG. 4. This was recorded on a solution of the antibiotic in deuterized methanol, using tetramethylsilane as the internal standard, on a Varian HR-SC spectrometer.

This invention further provides methods of combating, including prevention, relief and cure of, infections in human and other animals, which comprises administering a compound of the invention alone or in admixture with a carrier.

The antibiotic can be administered orally, parenterally (for example intramuscularly, intraperitoneally or intravenously), rectally or topically, preferably orally and parenterally, especially intramuscularly or intravenously. In general a satisfactory result is observed in both humans and other animals upon oral or parenteral administration of doses of from about 10 to about 1,000, preferably 5 to 600, mg/kg of body weight every 24 hours. Optionally this can be in the form of several individual administrations. A typical individual administration will be from about 50 to about 300, especially of 100 to 200, mg/kg of body weight. It can be necessary to deviate from these ranges and in particular to do so as a function of the nature and the severity of the illness, the nature of the preparation and of the administration of the medicine, and the time or interval over which the administration takes place. In some cases less than the above mentioned amount of active compound will be sufficient while in others the upper range must be exceeded. The optimum dosage and the administration must of course be based on the individual conditions, utilizing sound professional judgment.

The compound of the present invention is administered parenterally or orally in any of the usual pharmaceutical forms. These include solid and liquid oral unit dosage forms such as tablets, capsules, powders, suspensions, solutions, syrups and the like, including sustained release preparations, and fluid injectable forms such as sterile solutions and suspensions. The term unit dosage form as used in this specification and the claims refer to physically discrete units to be administered in single or multiple dosage to animals, each unit containing a predetermined quantity of active material in association with the required diluent, carrier or vehicle. The quantity of active material is that calculated to produce the desired therapeutic effect upon the administration of one or more of such units.

Powders are prepared by comminuting the compound to a suitable fine size and mixing with a similarly comminuted diluent pharmaceutical carrier such as an edible carbohydrate material as for example, starch. Sweetening, flavoring, preservative, dispersing and coloring agents can also be present.

Capsules are made by preparing a powder mixture as described above and filling formed gelatin sheaths. A lubricant such as talc, magnesium stearate and calcium stearate can be added to the powder mixture as an adjuvant before the filling operation; a glidant such as colloidal silica may be added to improve flow properties; a disintegrating or solubilizing agent may be added to improve the availability of the medicament when the capsule is ingested.

Tablets are made by preparing a powder mixture, granulating or slugging, adding a lubricant and disintegrant and pressing into tablets. A powder mixture is prepared by mixing the compound, suitably comminuted, with a diluent or base such as starch, sucrose, kaolin, dicalcium phosphate and the like. The powder mixture can be granulated by wetting with a binder such as syrup, starch paste, acacia mucilage or solutions of cellulosic or polymeric materials and forcing through a screen. As an alternative to granulating, the powder mixture can be run through the tablet machine and the resulting imperfectly formed slugs broken into granules. The granules can be lubricated to prevent sticking to the tablet forming dies by means of the addition of stearic acid, a stearate salt, talc or mineral oil. The lubricated mixture is then compressed into tablets. The medicaments can also be combined with free flowing inert carriers and compressed into tablets directly without going through the granulating or slugging steps. A protective coating consisting of a sealing cost of shellac, a coating of sugar or polymeric material and a polish coating of wax can be provided. Dyestuffs can be added to these coatings to distinguish different unit dosages.

Oral fluids such as syrups and elixirs can be prepared in unit dosage form so that a given quantity, e.g., a teaspoonful, contains a predetermined amount of the compound. Syrups can be prepared by dissolving the compound in a suitably flavored aqueous sucrose solution while elixirs are prepared through the use of a non-toxic alcoholic vehicle. Suspensions can be formulated by dispersing the compound in a non-toxic vehicle in which it is insoluble.

Fluid unit dosage forms for parenteral administration can be prepared by suspending or dissolving a measured amount of the compound in a non-toxic liquid vehicle suitable for injection such as an aqueous or oleaginous medium and sterilizing the suspension or solution. Alternatively a measured amount of the compound is placed in a vial and the vial and its contents are sterilized and sealed. An accompanying vial or vehicle can be provided for mixing prior to administration.

The antibiotic according to the invention is particularly active against bacteria and bacteria-like microorganisms such as Micrococaceae, such as Staphylococci, for example *Staphylococcus aureus, Staph. epidermidis, Staph. aerogenes* and *Gaffkya tetragena* (Staph. = Staphylococcus) Lactobacteriaceae, such as Streptococci, for example *Streptococcus pyogenes*, α- or β-haemolytic Streptococci, non-(γ)-haemolytic Streptococci, *Str. viridans, Str. faecalis* (enterococci), *Str. agalactiae, Str. lactis, Str. equi, Str. anaerobis* and *Diplococcus pneumoniae* (Pneumococci) (Str. = Streptococcus); Neisseriaceae, such as Neisseriae, for example *Neisseria gonorrhoeae* (Gonococci), *N. meningitidis* (Meningococci), *N. catarrhalis* and *N. flava* (N. = Neisseria); Corynebacteriaceae, such as Corynebacteria, for example *Corynebacterium diphtheriae, C. pyogenes, C. diphtheroides*. Enterobacteriaceae, such as Escherichiae bacteria of the coli group; Escherichia bacteria, e.g. *Escherichia coli, Klebsiella bacteria*, for example *K. pneumoniae*, Proteae bacteria of the Proteus group; Proteus, *Pr. mirabilis*, (Pr. = Proteus), Salmonelleae: Salmonella bacteria, for example *Salmonella paratyphi* A and B, *S. typhi, S. enteritidis, S. cholera suis* and *S. typhimurium* (S. = Salmonella), and Shigella bacteria, for example *Shigella dysenteriae*. Bacillaceae, such as aerobic spore-forming organisms, *B. subtilis* (B. = Bacillus) and anaerobic spore-forming organisms, Clostridia, for example *Clostridium perfringens, Cl. septicum, Cl. oedematiens, Cl. histolyticum, Cl. tetani* and *Cl. botulinum* (Cl. = Clostridium); and Mycoplasms, such as *Mycoplasma pneumoniae, M. Hominis, M. suis pneumoniae, M. gallisepticum* and *M. hyorhinis* (M. = Mycoplasma).

The above list of pathogens is purely illustrative and is in no way to be interpreted as restrictive.

Examples of conditions which can be treated include illnesses of the respiratory passages and of the pharyngeal cavity; otitis, pharyngitis, pneumonia, peritonitis, pyelonephritis, cystitus, endocarditis, systemic infections, bronchitis, arthritis, local inflammations and skin infections.

The antibiotic can also be used in animal breeding and livestock husbandry as an agent for promoting and accelerating growth and for improving the feedstuff utilization in healthy and sick animals. This activity is largely independent of the species and sex of the animals. The compound is particularly valuable in the raising and keeping of young animals and in fattening animals including warm-blooded mammals such as cattle, pigs, horses, sheep, goats, cats, dogs, rabbits, mink and chinchilla; poultry such as chickens, geese, ducks, turkeys, pigeons, parrots and canaries; and cold-blooded animals such as fish, for example, carp, and reptiles, for example snakes. The amount of the compound administered to the animals in order to achieve the desired effect can be varied substantially but generally is from about 5 to about 600, especially 10 to 300, mg/kg of body weight per day. The period of administration can be from a few hours or days up to several years. The amount of compound and the period of administration depend especially on the species, the age, the sex and the state of health of the animals as well as the manner in which the animals are maintained. The administration can be carried out orally or parenterally, once or several times daily, at regular or irregular intervals. For reasons of expediency, oral administration, especially through the intake of food and/or drink by the animals, is preferred in most cases. The compound can be administered as a pure substance or in the form of a formulation, as a mixture with non-toxic, inert carrier of any consumable type, and also in a formulation with other pharmaceutical active compounds, mineral salts, trace elements, vitamins, protein substances, fats, dyestuffs and/or flavorings.

The feed or drinking water can contain the active compound in a concentration of from about 5 to about 500, especially 10 to 100, ppm by weight. The optimum level of the concentration of the active compound in the feed or drinking water depends, in particular, on the intake of the animals and can be easily determined.

All the customary, commercially available or special feed compositions containing energy-giving and body-building substances, including vitamins and mineral substances, in the customary equilibrium required for balanced nutrition, can be used. The feed can be composed, for example, of vegetable substances, for example hay, beet, cereals and cereal by-products, animal substances, for example meat, fats, bonemeal and fish products, vitamins, for example vitamin A, D complex and B complex, proteins, amino-acids, for example DL-methionine, and inorganic substances, for example calcium carbonate and sodium chloride.

Feed concentrates will contain the active compound in addition to edible substances, for example rye flour, maize flour, soya bean flour or calcium carbonate, optionally with other nutrients and body-building substances as well as proteins, mineral slats and vitamins. These are prepared according to the customary mixing methods. In such premixes and feed concentrates, the active compound can be protected from air, light and/or moisture by suitable agents which cover its surface, for example by means of non-toxic waxes or gelatin.

A typical chick feed can contain 200 g of wheat, 340 g of corn, 361 g of shredded soya, 60 g of suet, 15 g of dicalcium phosphate, 10 g of calcium carbonate, 4 g of iodized sodium chloride, 7.5 g of a vitamin-mineral mixture and 2.5 g of active compound premix after careful mixing give 1 kg of feed. The vitamin-mineral mixture consists of: 6,000 I.U. of vitamin A, 1,000 I.U. of vitamin $D_3$, 10 mg of vitamin E, 1 mg of vitamin $K_3$, 3 mg of riboflavin, 2 mg of pyridoxine, 20 mcg of vitamin $B_{12}$, 5 mg of calcium pantothenate, 30 mg of nicotinic acid, 200 mg of choline chloride, 200 mg of $MnSO_4 \times H_2O$, 140 mg of $ZnSO_4 \times 7H_2O$, 100 mg of $FeSO_4 \times 7H_2O$ and 20 mg of $CuSO_4, \times 5 H_2O$. The active compound premix contains 20 mg of the active compound, 1 g of DL-methionine and sufficient soya bean flour to yield 2.5 g of premix.

A typical pig rearing feed can contain 630 g of shredded cereal feed (composed of 200 g of corn, 150 g of shredded barley, 150 g of shredded oats and 130 g of shredded wheat), 80 g of fish meal, 60 g of shredded soya, 60 g of tapioca meal, 38 g of brewers' yeast, 50 g of the above vitamin-mineral mixture, 30 g of linseed cake meal, 30 g of corn gluten feed, 10 soya oil, 10 g of cane sugar molasses and 2 g of the above active compound premix, which after careful mixing give 1 kg of feed.

The above feed mixtures are formulated for the rearing and fattening of chicks and pigs respectively but can, of course, also be used in the same or a similar composition for the rearing and fattening of other animals.

The antimicrobial activity of the antibiotic according to the invention can be conveniently observed in the following models:

a. In vitro

The antibiotic is diluted with Muller-Hinton nutrient liquor, with the addition of 1% of glucose, to a content of 300 µg/ml. The nutrient solution contained, in each case, $1 \times 10^5$ to $2 \times 10^5$ bacteria per milliliter. Test tubes containing this charge were in each case incubated for 18 hours and the degree of turbidity was then determined. Freedom from turbidity indicates action. At a level of 300 µg/ml, freedom from turbidity can be observed with such diverse bacterial cultures as Escherichia coli 14; Proteus vulgaris, 1017; Klebsiella 8085; Salmonella sp.; Proteus mirabilis sp; Pasteurella pseudotuberculosis; Staphylococcus aureus 133; Neisseria catarrhalis sp; Diplococcus pneumoniae sp.; Streptococcus pyogenes W; Lactobacillus sp.; Corynebacterium diphtheriae gravis; Mycoplasma sp. (Sp. = "species" — not identified more precisely, but characteristic strains).

b. In vivo

Table 4 shows the action of the antibiotic against bacterial infections in white mice. $CF_1$ strain white mice were infected intraperitoneally with the bacterial indicated one administration of the antibiotic was given subcutaneously 30 minutes after infection. The $ED_{50}$ is given as the dose at which 50% of the injected animals survive after 24 hours.

Table 4

|  | $ED_{50}$ |
|---|---|
| Escherichia Coli 165 | 400 mg |
| Staphylococcus aureus | 200 mg |

The activity of the antibiotic as an agent for promoting growth can be demonstrated in feeding tests in which the substance is mixed into the feed and fed to chicks at a concentration of 10 and 25 ppm for 14 days. A comparison is made against a negative control (feed without additives).

Table 5

|  | Number of animals | Average weight (g) | % Weight |
|---|---|---|---|
| Control | 24 | 358.2 | 100 |
| Antibiotic |  |  |  |
| 10 ppm | 24 | 372.5 | 104.0 |
| 25 pm | 24 | 383.7 | 107.1 |

The present antibiotic thus couples a low toxicity with strong microbial activity. These properties permit its use not only as a chemotherapeutic agent but also as a compound for preserving inorganic and organic materials, in particular organic materials of all kinds, for example polymers, lubricants, paints, leather, paper and timber, foodstuffs and water.

The preparation of the antibiotic according to the invention can be illustrated by the examples which follow in which all the percentage data relate, unless otherwise stated, to percentages by weight.

EXAMPLE 1

Mycelium of the strain Actinoplanes SE-73/B cultured on slant agar of the composition (percentages by weight)

| peptone | 0.25% |
|---|---|
| acid hydrolysed casein | 0.25% |
| $K_2HPO_4 \times H_2O$, p.a. | 0.1% |
| KCl, p.a. | 0.05% |
| $MgSO_4$, p.a. | 0.05% |
| $FeSO_4$, p.a. | 0.01% |
| cane sugar | 3.0% |
| agar | 2.0% |
| water to make up to | 100% | was used to inoculate 140 ml samples, in 1 liter conical flasks of sterile nutrient solution (termed "nutrient solution A" in the following test) of the composition

| soya flour, defatted | 3.0% |
|---|---|
| glycerol, very pure | 3.0% |
| $CaCO_3$, p.a. | 0.2% |
| water to make up to | 100 % | plus, for defoaming, 1 drop/140 ml of nutrient solution of neutral polyol containing hydroxyl groups, for example Niax Polyol LHT 67 (trademark of Union Carbide Belg. N.V.). After cultivating the strain for 8 days on a circular shaking machine at 28° C, samples of the cultures were centrifuged. The clear, supernatant solution was tested against Escherichia coli ATCC 9637 in the agar plate diffusion test. The antibiotic according to the invention which was present in the culture solution produced zones of inhibited growth about 17 mm in diameter. The antibiotic according to the invention was isolated from the culture broths as described in Example 3.

EXAMPLE 2

In each case, 8 liters of nutrient solution of the composition (percentages by weight)

| dextrin | 0.4% |
|---|---|
| glycerol | 0.2% |
| yeast extract | 0.2% |
| $CaCO_3$ | 0.2% |
| tap water to make up to | 100 % | and 3.0 ml of neutral polyol containing hydroxyl groups (for example Niax Polyol LHT 67 (trademark of Union Carbide Belg. N.V.) per 8 liters of nutrient solution were introduced into glass fermenters with a stirrer and an aeration device. The pH was adjusted to 6.8 sodium hydroxide solution and the mixtures were sterilized at 120° C. After the solutions had cooled, the fermenters werer inoculated with, in each case, 240 ml. (3.0% by volume) of shaking cultures of the Actinoplanes strain SE-73 (which had been grown for 3 days in nutrient solution A) and aerated with about 4 liters of air/minute, with stirring at about 600 revolutions per minute, and maintained at a temperature of 28° C. 17 and 24 hours after the start of cultivation, additions of, in each case, 0.4% of dextrin, 0.2% of glycerol and 0.3% of yeast extract were made to the fermenters and after 30, 41, 48 and 54 hours additions of, in each case, 0.4% dextrin, 0.2% of glycerol and 0.4% of yeast extract were made. These additions were in the form of concentrated mixtures of these nutrient solution components in a volume of, in each case, 200 ml per addition. An increase in the volumes of the cultures due to these additions was compensated by the evaporation of water. The total amounts of the nutrient solution components which were provided were 2.8% in the case of dextrin, 1.4% in the case of glycerol, 2.4% in the case of yeast extract and 0.2% in the case of $CaCO_3$. The cultivation was ended after 120 hours.

EXAMPLE 3

The culture broths obtained according to Example 2, from 5 glass fermenters (5 × 8 liters) were combined, 48 liters of acetone were added and the mixture was stirred for one hour at about 25° C and then centrifuged. The clear supernatant liquid, freed from the extracted mycelium, is concentrated in vacuo at 20° to 35° C to about 35 liters, the pH was adjusted to 9 with sodium hydroxide solution and the mixture was extracted with 18 liters of ethyl acetate.

The pH of the residual aqueous solution was adjusted, after saturation with sodium chloride, to 8.5 with sodium hydroxide solution and the mixture was extracted with two 9 liter volumes of ethyl acetate. The organic extracts were concentrated in vacuo to about 1 liter and the crude antibiotic was precipitated from this solution by the addition of 3 liters of n-hexane. The precipitate was collected by filtration, washed with a little ether and introduced into water with stirring, a pH value of 7.3 being maintained through the addition of 10% strength sodium carbonate solution. 10.5 g of the crude antibiotic (containing a little sodium carbonate) were obtained from this solution by lyophilization.

EXAMPLE 4

When the crude antibiotic obtained according to Example 3 was subjected to analytical thin layer chromatography, the dyestuffs remained at the starting point and the antibiotic according to the invention was in the uppermost zone using 5:1 chloroform:methanol (by volume) as the flow agent of F 254 silica gel plates (Merck, Darmstadt).

1.00 g of the crude antibiotic were subjected to preparative layer chromatography on 20 silica gel plates (Merck F 254, 2 mm) using 5:1 chloroform:methanol (by volume) as the flow agent. The uppermost zone which is visible under UV, was isolated to yield 344 mg. Antibiotic activity in the plate test against *Escherichia coli* ATCC 9637 was 152% of that of the crude starting material.

EXAMPLE 5

10 g of the crude antibiotic obtained according to Example 3 were dissolved in 600 ml of twice distilled water and filtered through an acetylated polycaprolactam (MN-polyamide SC-6 Ac, Macherey, Nagel & Co.), in a column 70 cm in length and 5 cm in diameter. The fraction which absorbed at 267 nm were collected. The main fraction was extracted with chloroform, the chloroform solution was evaporated and the residue was dried at 60° C/0.01 mm Hg for 4 days to yield 5.2 g. Antibiotic activity in the plate test against *Escherichia coli* ATCC 9637 was 148% of that of the starting material.

EXAMPLE 6

1.00 g of the crude antibiotic obtained according to Example 3 was dissolved in 100 ml of acetone. Cyclohexane was added in portions to the solution, which had been clarified by centrifuging, and the resulting sediment was isolated by centrifuging.

| Ml of cyclohexane added | Precipitate in mg | % activity plate test - E.coli |
|---|---|---|
| + 10 | 43 | 69 |
| + 28 | 125 | 119 |
| + 17 | 182 | 135 |
| + 25 | 157 | 109 |
| + 60 | 120 | 115 |

This fractionation method could be further optimized by systematic variation of the solvents.

The purified antibiotic gave the following analytical values: C 50.8%; H 7.2%; and O 42.0%. The analytical values can be subject to an error of about ± 1% in each case.

The plate diffusion test mentioned in the examples was carried out as follows: holes were punched in to an agar plate culture of *Escherichia coli* ATCC 9637. The material to be tested was placed as an aqueous solution into these holes. The plate was then incubated at 37° C for about 16 hours. A zone of inhibition indicated activity against the microorganism used, the content of the antibiotic being determined from the size of the zone of inhibition.

What is claimed is:

1. An antibiotic characterized by being a neutral solid which does not migrate upon electrophoresis; contains carbon, hydrogen and oxygen in the weight ratio of carbon to hydrogen to oxygen of 50.8:7.2:42 respectively; is soluble in water, lower alcohols, chloroform and acetone and sparingly soluble in diethyl ether, petroleum ether and cyclohexane; is optically active with the specific rotation value $[\alpha]_D^{20}$ measured as a 1% solution in methanol being −32.97°; has a pronounced UV absorption band at 267 mm with an $E^{1\%}$/cm of 164; and exhibits characteristic absorption at the following infrared frequencies expressed in reciprocal centimeters: 3440, 2960, 2920, 2850, 1630, 1570, 1445, 1405, 1375, 1310 (weak), 1290 (weak), 1200, 1060, 1020, 895, 940, 905, 780 and 750.

2. Process for the preparation of the antibiotic according to claim 1 which comprises aerobically cultivating in a culture medium containing assimilable sources of carbon, nitrogen and minerals, Actinoplanes ATCC No. 31058 or ATCC No. 31060 at a pH of from about 6 to about 8 and at a temperature of from about 20° to about 40° C until a substantial amount of antibiotic activity is produced by the organism in said culture medium, and isolating from the culture medium the antibiotic as defined in claim 1 thus produced.

3. Process according to claim 2 wherein said antibiotic is isolated through extraction of said culture with an organic solvent in which said antibiotic is soluble.

4. The process according to claim 2 wherein said Actinoplanes ATCC Nos, 31058 or 31060 is cultivated at a temperature of from about 25° to about 35° C until aliquots of the culture solution demonstrate substantial antibiotic activity, the culture solution is extracted with a water miscible organic solvent to separate said antibiotic from said culture solution, and said antibiotic is purified by one or more of solvent extraction, precipitation and chromatography.

5. The method of combatting bacterial infections in humans and other animals which comprises administering to a human or other animal an antibacterially effective amount of the antibiotic according to claim 1.

6. An antibacterial pharmaceutical composition comprising an antibacterially effective amount of the antibiotic according to claim 1 in combination with a pharmaceutically acceptable carrier.

7. Antibacterial pharmaceutical composition according to claim 1 adapted for oral or parenteral administration.

8. A composition for promoting growth in livestock comprising a nontoxic consumable carrier in combination with an amount of the antibiotic according to claim 1 which when consumed with said carrier or when further diluted in predetermined proportion with drinking water or feed is sufficient to effectively promote growth in said livestock.

9. The method of promoting growth in livestock which comprises administering to livestock at least a growth promoting amount of the antibiotic according to claim 1.

* * * * *